United States Patent [19]

Toyama

[11] Patent Number: Plant 7,035

[45] Date of Patent: Sep. 19, 1989

[54] APRICOT TREE PA 7221-1

[75] Inventor: Thomas K. Toyama, Prosser, Wash.

[73] Assignee: Washington State University Research Foundation, Pullman, Wash.

[21] Appl. No.: 223,898

[22] Filed: Jul. 21, 1988

[51] Int. Cl.[4] ..... A01H 5/00

[52] U.S. Cl. ..... Plt./39

[58] Field of Search ..... Plt./39

*Primary Examiner*—Robert E. Bagwill

*Attorney, Agent, or Firm*—Chernoff, Vilhauer, McClung & Stenzel

[57] ABSTRACT

A new variety of apricot tree of large and medium dense growth is a regular and productive bearer of very large size, firm, orange fleshed, freestone fruits. The attractive fruits are light orange in color overlaid by a reddish purple blush, have excellent eating quality and are capable of being shipped to long distance fresh markets.

2 Drawing Sheets

BACKGROUND AND SUMMARY OF THE INVENTION

The present invention relates to a new and distinct variety of apricot tree which is a regular and productive bearer of very large size, firm, oranged fleshed, freestone fruits. The fruits are light orange in color overlayed by a reddish-purple blush, have excellent eating quality, and can be shipped to long distance fresh markets.

This new variety of apricot tree was originated at the Irrigated Agriculture Research and Extension Center at Prosser, Wash. from crosses made in 1972. It was selected in 1975 from several seedlings which were derived from the cross Goldrich (unpatented) and a known but unnamed seedling selection of Earliril×-Blenril (both varieties unpatented). Second test trees were planted on the Roza unit of the center in 1977 and came into production in 1980.

Flowers of the present variety require cross-pollination. They will set fruits with pollen of one of their parents (the Goldrich variety), Perfection (unpatented), and Rival (unpatented). In addition, flowers of the subject variety are pollinated by and will pollinate flowers of Apricot Tree PA 7201-1 which is the subject of a patent application filed concurrently herewith.

Trees of the subject variety are large, vigorous, and dense in growth habit. The fruits ripen about two weeks before Wenatchee (unpatented) in the Yakima Valley of Washington. It is round to slightly oval in shape and is very large, being up to 2⅝ inches in diameter when adequately thinned. The skin is light orange and slightly glossy in appearance and has an attractive reddish-purple blush covering up to 20% of its surface. The flesh is firm and moderately juicy. Some acidity is associated with the skin. The fruits are large, firm and attractive and are of excellent quality and flavor. The fruits most nearly resemble those of Apricot Variety PA 7201-1. These two new apricot varieties are meant to be planted together in the orchard as sister varieties since they cross-pollinize one another and produce similar fruits which mature at the same time. Thus the fruits can be harvested, packed, and shipped together.

Trees of the subject variety are vigorous on both apricot and peach seedling rootstocks. They bloom heavily but often tend to set only relatively light crops, thereby reducing the need for hand thinning. The extra large attractive fruits can be readily trade packed to premium fresh markets.

Asexual reproduction of this new and distinct variety shows that its unique characteristics come true to form and are established and transmitted through succeeding propagations by grafting.

BRIEF DESCRIPTION OF THE DRAWINGS

In the accompanaying photographs, vegetative growth and fruit of the new variety are shown both on and off the tree and are depicted in color as nearly true as is reasonably possible to make in color illustration of this character.

DETAILED DESCRIPTION OF THE DISCLOSURE

Figure 1:
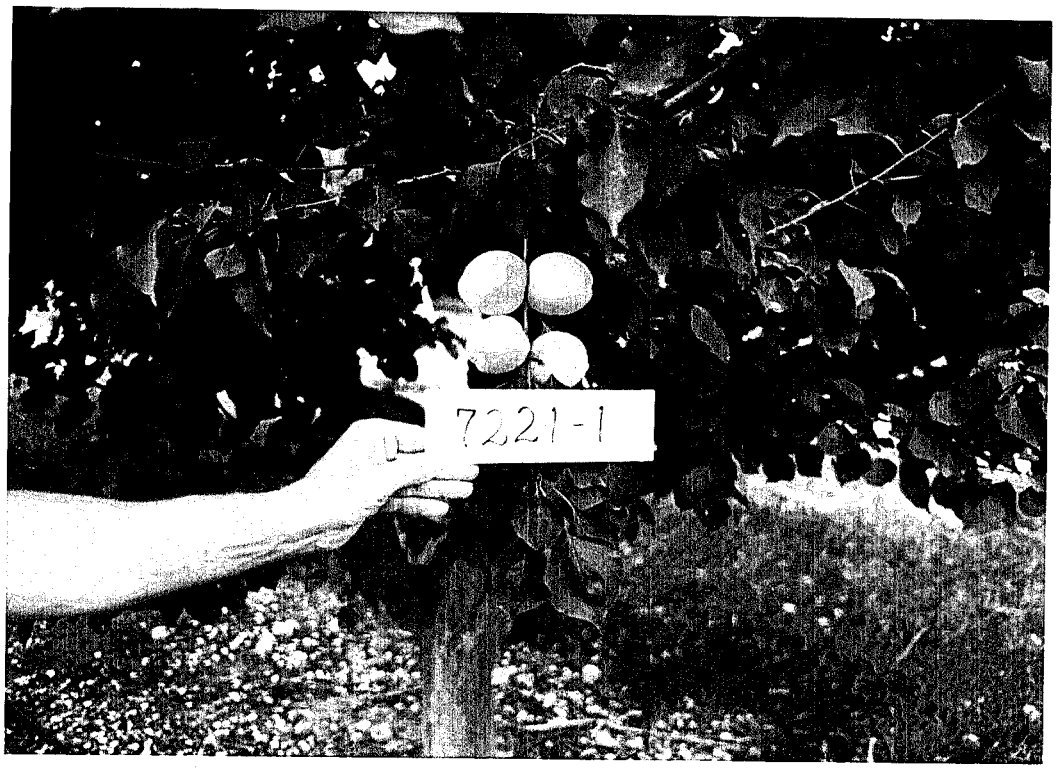
FIG. 1 shows the vegetative growth and fruits of a mature specimen of the subject variety on the tree.
Figure 2:
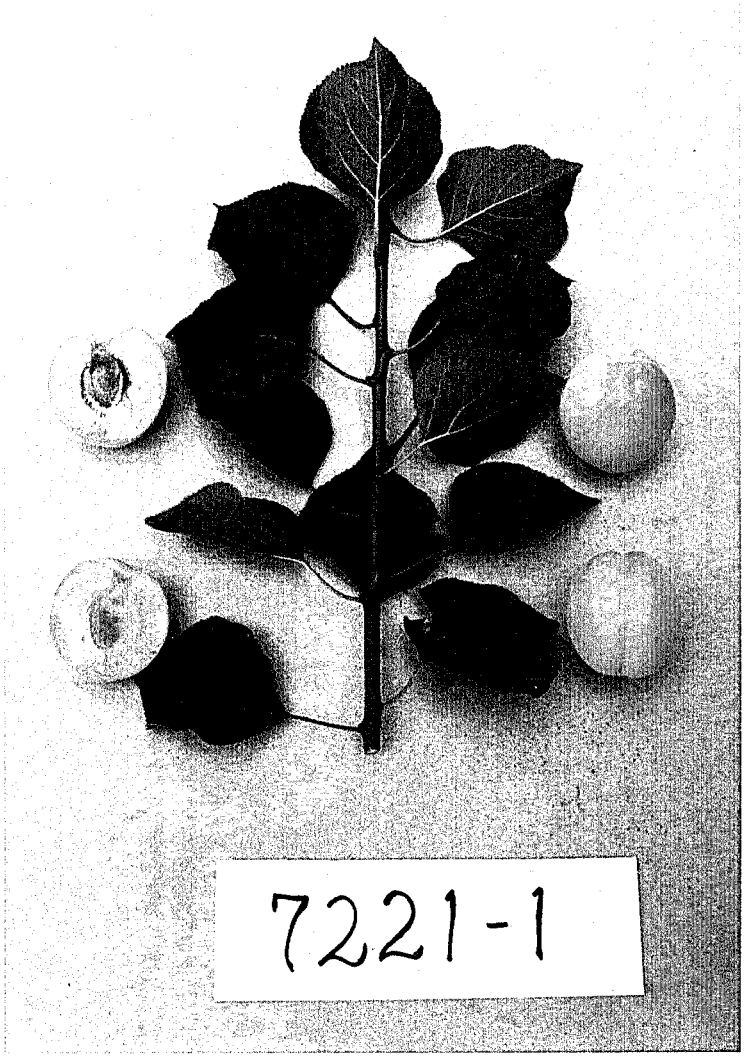
FIG. 2 shows the stems and leaves along with the whole and half fruits of the subject variety off of the tree.

The following description was based on observations made of four six-year-old second generation trees growing at the Irrigated Agriculture and Research Station at Prosser, Wash. and of four five-year-old trees growing in a variety test plot at Parker, Wash. Color designations are to a Munsell Color Cascade Chart except where general color terms of ordinary dictionary significance are used.

Tree:
- *Size.*—Large.
- *Vigor.*—Vigorous.
- *Growth.*—Upright, then spreading.
- *Density.*—Medium dense.
- *Production.*—Productive.
- *Bearing.*—Regular.

Trunk:
- *Size.*—Stocky.
- *Texture.*—Medium.

Branches:
- *Size.*—Medium stocky.
- *Lenticels.*—Medium size, medium number.
- *Texture.*—Smooth.
- *Color.*—Brown (29-14) to reddish brown (30-12).

Leaves:

*Size.*—Large, average length $3\frac{1}{8}$ inches to $3\frac{3}{4}$ inches, average width $2\frac{3}{4}$ inches to $3\frac{5}{8}$ inches.
*Shape.*—Ovate to orbicular, pointed.
*Petiole.*—Average length, average thickness.
*Glands.*—Average number and position, 3–5 on petiole and 2 on blade, small, globose, alternate, greenish.
*Margin.*—Finely serrate.
*Color.*—Upper surface — green (20-13), lower surface — light green (20-10).

Flower buds:
*Size.*—Medium.
*Length.*—Medium.
*Shape.*—Conical, plump.
*Surface.*—Lightly pubescent.

Flowers:
*Date of bloom.*—Full bloom March 24, ripe July 9.
*Size.*—Large, $1\frac{1}{8}$ inches in diameter.
*Color.*—Pinkish before flowers open, almost completely white at full bloom.
*Pubescence.*—Very slight.
*Number of pistils.*—One.
*Number of stamens.*—Average 24 to 26.

Fruit:
*Maturity.*—About 2 weeks before Wenatchee, about July 10 at Prosser.
*Size.*—Uniformly large, Diameter — $2\frac{1}{2}$ inches to $2\frac{5}{8}$ inches, transverse in suture plane — $2\frac{1}{2}$ inches to $2\frac{5}{8}$ inches, transverse at right angles to suture plane $2\frac{1}{8}$ inches to $2\frac{1}{2}$ inches.
*Form.*—Uniform, round, oval.
*Suture.*—Distinct, extends from base to apex.
*Cavity.*—Rounded, slightly elongate in suture plane, shallow, average depth $\frac{1}{4}$ inch, average breadth $\frac{3}{8}$ inch.
*Base.*—Smoothly rounded on dorsal side, abruptly rounded on suture side.
*Apex.*—Slightly rounded.
*Pistil point.*—Slightly depressed.
*Stem.*—Length $\frac{1}{4}$ inch, Caliper $\frac{1}{8}$ inch.

*Skin.*—Smooth, glossy, medium texture, medium thickness.
*Tendency to crack.*—None.
*Down.*—Scant, short.
*Color.*—Light orange ground (32-8), reddish-purple blush (43-12) on side exposed to sun.
*Tenacity.*—Tenacious to flesh.

Flesh:
*Uniformity.*—Uniform, ripening only slightly earlier at apex.
*Texture.*—Firm, fine grained, meaty.
*Surface of Pit Cavity.*—Smooth.
*Juice.*—Slightly juicy.
*Flavor.*—Sweet, sub-acid, strong flavor distinction.
*Aroma.*—Aromatic, very distinct.
*Color.*—Apricot orange (30-8).
*Eating quality.*—Very good.

Stone:
*Type.*—Freestone.
*Size.*—Medium large, average length $1\frac{1}{8}$ inches, average breadth 1 inch, average thickness $\frac{5}{8}$ inch.
*Form.*—Ovoid, slightly cuneate toward apex.
*Sides.*—Very sightly pitted.
*Dorsal suture.*—Full, with shallow groove toward base and apex.
*Color.*—Varies slightly, from light brown (28-13) to brown (28-14).
*Tendency to split.*—None.

Use: Fresh, local and long distance markets.
Keeping quality: Very good.
Shipping quality: Very good.

What is claimed is:

1. A new and distinct variety of apricot tree obtained as a seedling from a seed parent entitled Goldrich (unpatented) and a pollen parent which is an unnamed seedling selection of Earliril × Blenril (both unpatented) is characterized by its vigorous and medium dense growth and its large, firm, attractive, and flavorful fruits which are suited particularly for shipment to distant fresh markets.

* * * * *

UNITED STATES PATENT AND TRADEMARK OFFICE

CERTIFICATE OF CORRECTION

PATENT NO. : PP7035

DATED : September 19, 1989

INVENTOR(S) : Thomas K. Toyama

It is certified that error appears in the above-identified patent and that said Letters Patent is hereby corrected as shown below:

Col. 4, line 23 Change "sightly" to --slightly--

Signed and Sealed this

Twenty-eighth Day of July, 1992

*Attest:*

DOUGLAS B. COMER

*Attesting Officer*

*Acting Commissioner of Patents and Trademarks*